United States Patent [19]
Nohda

[11] Patent Number: 4,572,628
[45] Date of Patent: Feb. 25, 1986

[54] METHOD OF AND APPARATUS FOR MEASURING RADIUS

[75] Inventor: Masao Nohda, Yokosuka, Japan

[73] Assignee: Nippon Kogaku K.K., Tokyo, Japan

[21] Appl. No.: 379,552

[22] Filed: May 18, 1982

[30] Foreign Application Priority Data

May 29, 1981 [JP] Japan .................................. 56-82023
May 29, 1981 [JP] Japan .................................. 56-82024

[51] Int. Cl.$^4$ .......................................... A61B 3/10
[52] U.S. Cl. ..................................... 351/212; 351/221
[58] Field of Search ............... 351/211, 212, 219, 220, 351/221; 356/124, 125, 127, 376

[56] References Cited

U.S. PATENT DOCUMENTS 3,781,096 12/1973 Townsley ............................ 351/212
4,312,574 1/1982 Wilms ................................. 351/212

Primary Examiner—Rodney B. Bovernick
Assistant Examiner—Paul Dzierzynski
Attorney, Agent, or Firm—Shapiro and Shapiro

[57] ABSTRACT

A method of measuring the radius of curvature of an object to be examined has a first procedure of projecting two pairs of light spots onto the object from different directions, a second procedure of obtaining by an imaging optical system the reflected images of the two pairs of light spots reflected by the object, and a third procedure of measuring the radius of curvature of the object from the positional relation between the reflected images by the imaging optical system. An apparatus for carrying out this method includes measuring optical means having an objective lens, first projection optical means for projecting a pair of light spots onto an object to be examined from a direction symmetric to the optical axis of the objective lens, second projection optical means for projecting a pair of light spots onto the object from a direction symmetric to the optical axis of the objective lens and discrete from the first projection optical system, photoelectric converting means for producing signals corresponding to at least three projection spacings in which the spacing between the images of each of said pairs of light spots has been projected in two predetermined directions at a predetermined position on the optical axis of the measuring optical system and in a plane orthogonal to said optical axis, and operation display means for determining and displaying the directions of the principal meridians of the object and the radii of curvature in those directions from said at least three projection spacings measured by the apparatus.

6 Claims, 22 Drawing Figures

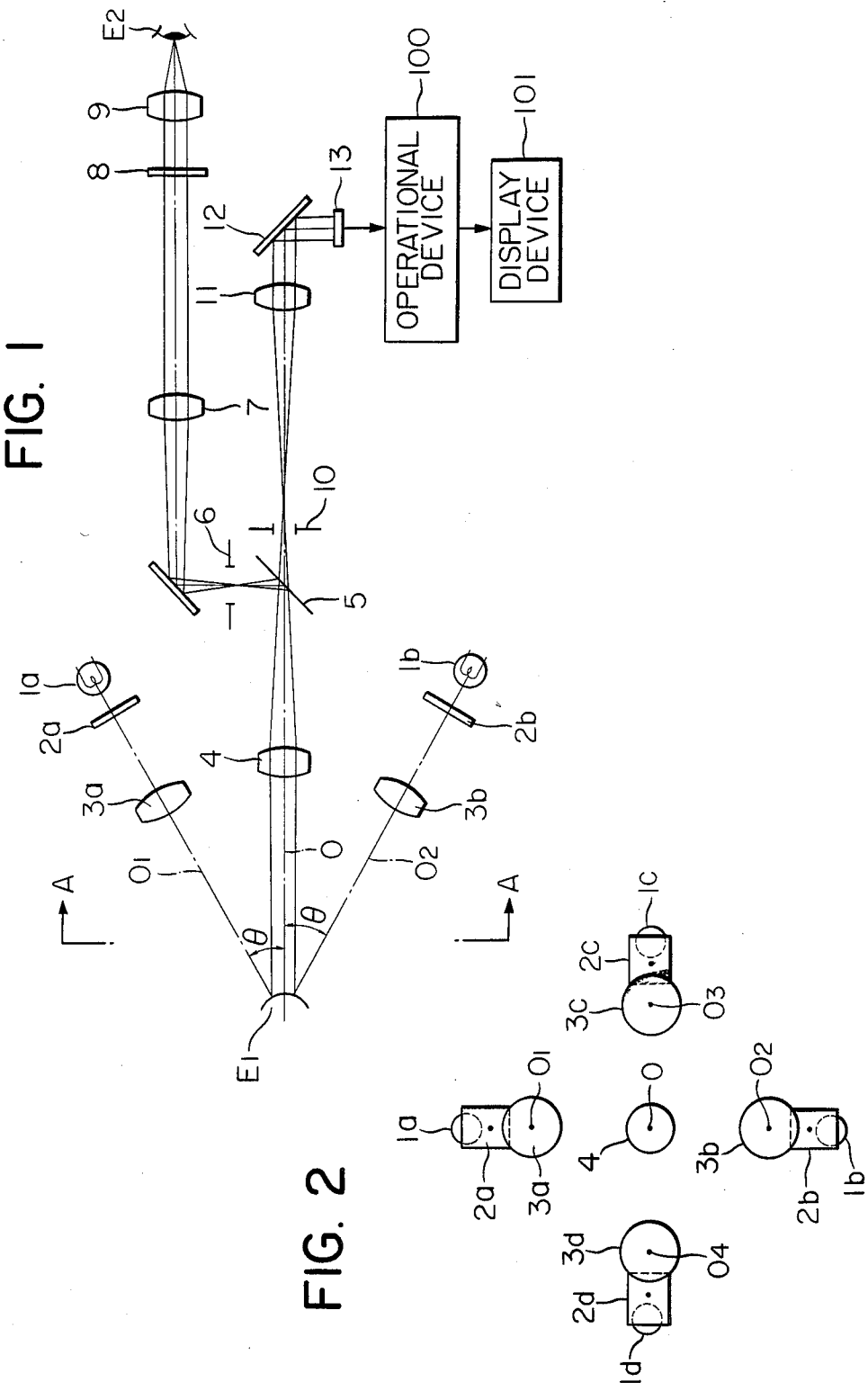

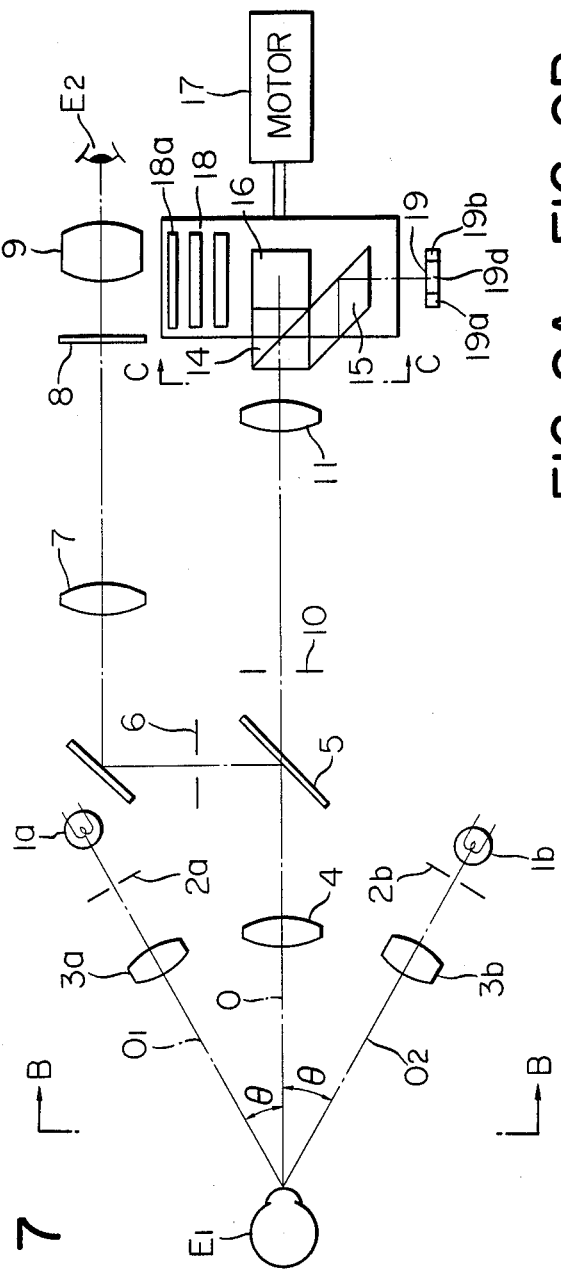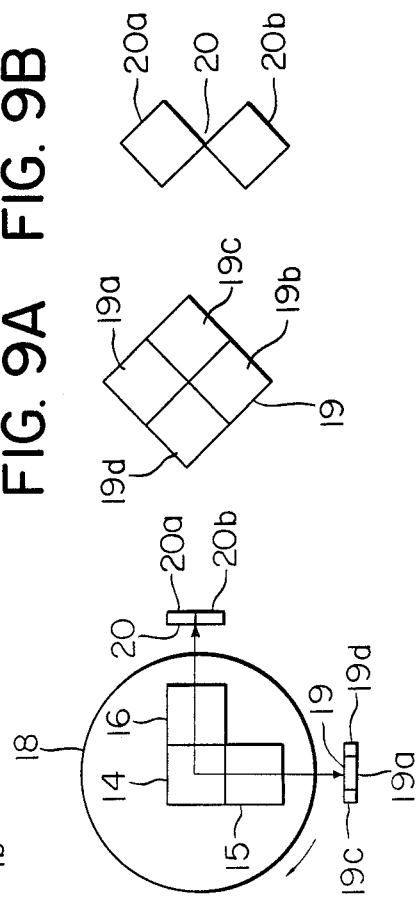

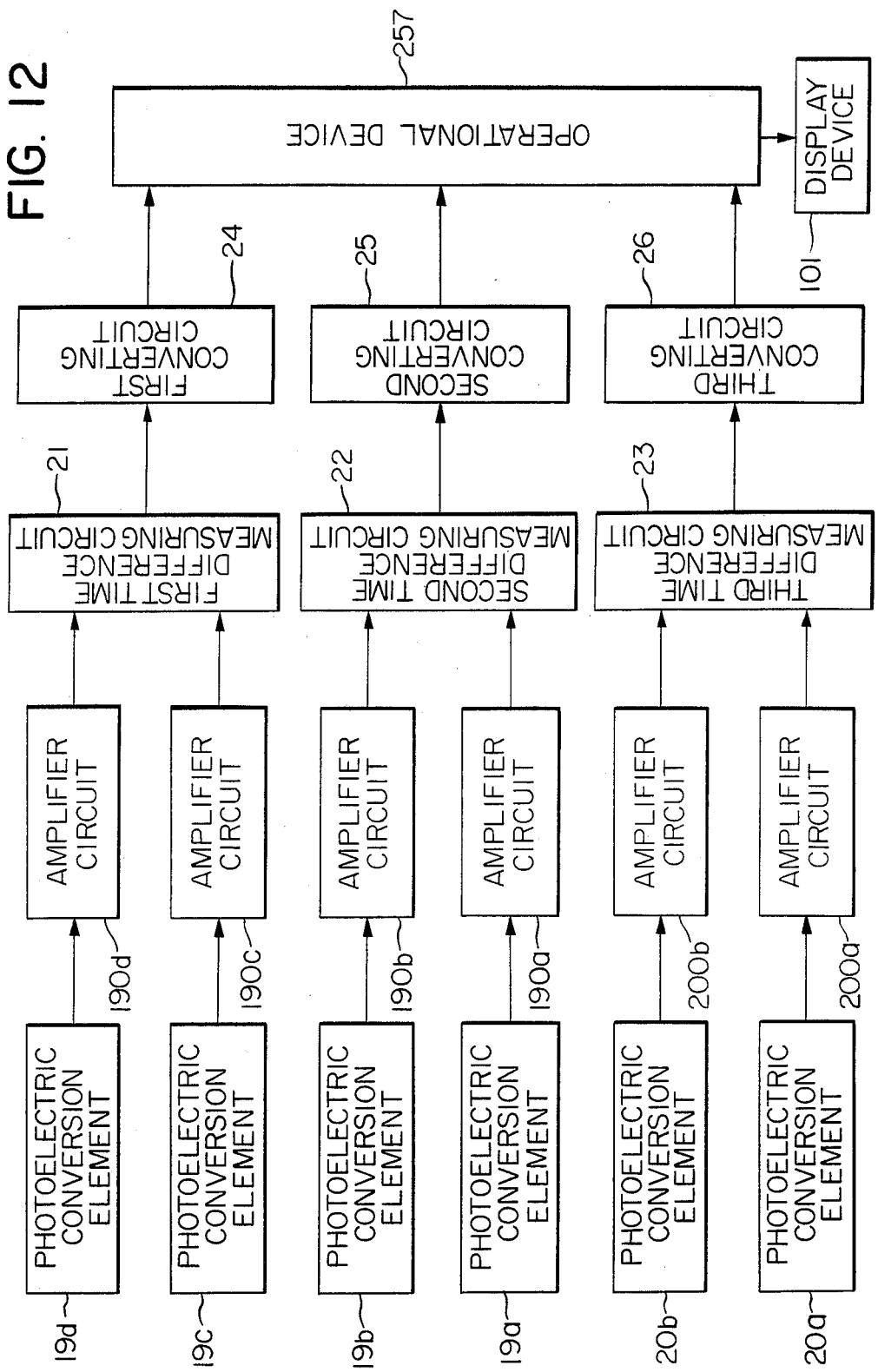

METHOD OF AND APPARATUS FOR MEASURING RADIUS

BACKGROUND OF THE INVENTION

1. Field of the Invention

This invention relates to a method of and an apparatus for measuring the radius of curvature of a cornea, a lens or the like, and more particularly to a simple method of and a simple apparatus for measuring the directions of two principal meridians of an object to be examined including a toric surface and the radii of curvature in those directions.

2. Description of the Prior Art

As a general method of measuring a radius of curvature, there is known a method comprising projecting onto an object to be examined two object projecting light spots disposed at the opposite sides of the optical axis of an objective lens, obtaining the spacing between the reflected images of the light spots formed at predetermined positions in a measuring optical system including the objective lens, and measuring the radius of curvature of the object from this spacing. In this method, where the object is a spherical surface, the spacing between the reflected images directly corresponds to the radius of curvature of the object, but where the object includes a toric surface, the spacing between the reflected images does not directly correspond to the values corresponding to the radii of curvature in the directions of two principal meridians as the measured values. This is because, where the object includes a toric surface, the direction in which the reflected images are created is twisted by a predetermined amount in accordance with the projection directions of the light spots relative to the direction in which the reflected images are created where the object is a spherical surface (the direction passing through the two reflected images). In the method according to the prior art, attention is paid to the fact that the above-mentioned twist does not occur if the projection directions of the light spots are coincident with the directions of the principal meridians of the object, and the curvatures in the directions of the two principal meridians are obtained from the spacing between the reflected images created when said coincidence has occurred.

In a specific example using such method, if the standard line overlapping the two reflected images created when the object is, for example, a spherical surface is made observable from the viewfinder and the design is such that the two reflected images and the standard line overlap each other by the entire apparatus being rotated and the then spacing between the reflected images is optically or photoelectrically obtained and the then rotated position of the apparatus is obtained, then the radius of curvature and the amount of twist in the direction of one principal meridian will be obtained. The radius of curvature in the direction of the other principal meridian will be obtained if the apparatus is rotated by 90° and the spacing between the two reflected images at that time (when of course the two reflected images and the standard line are overlapping each other) is obtained.

However, in the above-described measuring method according to the prior art, whether the object to be examined is a spherical surface or a toric surface cannot be discriminated by the measurement only in the direction of one meridian and accordingly, it is necessary to effect measurement in the directions of two meridians and this is time-consuming and, where the object to be examined is a toric surface, it is necessary to measure the spacing between the reflected images in the directions of two principal meridians and the direction of at least one principal meridian and thus, the measurement has been cumbersome.

In any case, the measuring method according to the prior art has involved a number of measuring procedures and has not been preferred as a curvature-radius measuring method when simplicity is desired.

SUMMARY OF THE INVENTION

It is an object of the present invention to provide a method capable of very simply measuring the radius of curvature of an object to be examined and an apparatus which puts such method into practical use.

The invention will become fully apparent from the following detailed description thereof taken in conjunction with the accompanying drawings.

BRIEF DESCRIPTION OF THE DRAWINGS

FIG. 1 is a side view of chiefly the optical system of a first embodiment of the present invention.

FIG. 2 is a view taken along arrow A—A of FIG. 1.

FIG. 7 is a side view of chiefly the optical system of a second embodiment of the present invention.

FIG. 8 is a view taken along arrow C—C of FIG. 7.

FIGS. 9A and 9B are plan views of photoelectric converting devices used in FIG. 8.

FIG. 12 is a block diagram of the circuit for processing the output signals of the photoelectric conversion elements.

DESCRIPTION OF THE PREFERRED EMBODIMENTS

Figure 3A:
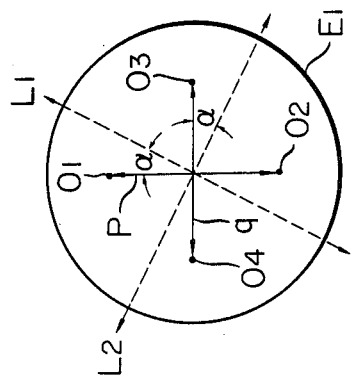
FIGS. 3A to 3C illustrate the manner in which the images of the pin-hole plates of the FIG. 1 apparatus enter an eye to be examined in each case.

Described first as an example is a case where a mark is a pair of light spots and two planes each containing a pair of projection optical systems are orthogonal to each other and a pair of standard directions determined in a plane orthogonal to the optical axis of a measuring optical system in a predetermined position thereof are determined so as to be orthogonal to each other. When a spherical surface is used as an object to be examined, the pair of standard directions may overlap the images of the pair of light spots. FIG. 1 shows an example of the optical system of an ophthalmometer for realizing the method of the present invention.

In FIG. 1, in order that a pair of light spots may be projected onto an eye $E_1$ to be examined from directions symmetric to the optical axis O of the objective lens 4 of a measuring optical system, the optical axes $O_1$ and $O_2$ of a pair of projection optical systems are formed in a plane containing the optical axis O of the objective lens (the plane of the drawing sheet of FIG. 1). Both of the angles formed by the projection optical axes $O_1$ and $O_2$ with the optical axes O of the objective lens are $\theta$. The light beams emitted from illuminating light sources 1a and 1b on the optical axes $O_1$ and $O_2$ pass through pin-hole plates 2a and 2b and thereafter are collimated into parallel beams by collimator lenses 3a and 3b whose focal planes are on the pin-hole plates 2a and 2b, whereafter they are projected onto the eye $E_1$ to be examined.

As can be seen from FIG. 2 which is a view taken along arrow A—A of FIG. 1 and showing the optical system of FIG. 1 as seen from the eye $E_1$, the optical axes $O_3$ and $O_4$ of a pair of projection optical systems are also formed in a plane containing the optical axis O of the objective lens and orthogonal to the plane of the drawing sheet of FIG. 1 in order that a pair of light spots may be projected onto the eye $E_1$ from directions symmetric to the optical axis O of the objective lens. Both of the angles formed by the projection optical axes $O_3$ and $O_4$ with the optical axis O of the objective lens are $\theta$. Of course, in the present example, the projection optical axes $O_1$, $O_2$, $O_3$ and $O_4$ are disposed so as to intersect one another at a point on the optical axis O of the objective lens. The projection optical systems lying in the plane perpendicular to the plane of the drawing sheet of FIG. 1, like the projection optical systems shown in FIG. 1, respectively have illuminating light sources 1c and 1d, pin-hole plates 2c and 2d, and collimator lenses 3c and 3d on their respective optical axes $O_3$ and $O_4$.

The measuring optical system is separated into an automatic measuring light path and an observation light path of an examiner $E_2$ by a beam splitter 5. The pre-objective lens 4 is common to the two light paths, and a post-objective lens 7 which constitutes a telecentric system together with the objective lens 4 is provided in the observation light path reflected from the beam splitter 5, and a diaphragm 6 is provided in a plane on which the rearward focal plane of the pre-objective lens 4 and the forward focal plane of the post-objective lens 7 are coincident with each other. The image formed on a focusing screen 8 by the objective lenses 4 and 7 may be observed by the examiner $E_2$ through an eyepiece 9.

A post-objective lens 11 which constitutes a telecentric system together with the objective lens 4 is provided in the automatic measuring light path passed through the beam splitter 5, and as in the case of the above-described observation optical system, a diaphragm 10 is provided in a plane on which the rearward focal plane of the objective lens 4 and the forward focal plane of the post-objective lens 11 are coincident with each other. The light path from the objective lens 11 is bent at 90° by a mirror 12, whereafter it enters a photoelectric converter device 13. The photoelectric converter device 13 is a light image position detector comprising for example, small light receiving elements (photoelectric conversion elements) arranged two-dimensionally, and the light receiving surface thereof is disposed so as to be perpendicular to the light paths of the objective lenses 4 and 11. The photoelectric converter device 13 can produce on the light receiving surface thereof a signal corresponding to the position of the pin-hole image created by the objective lenses.

Figure 4A:
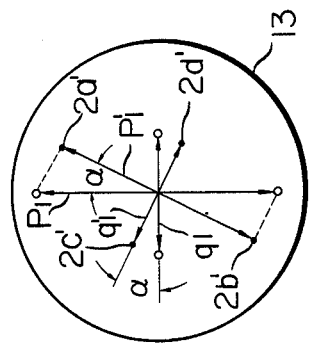
FIGS. 4A to 4C illustrate the manner in which the images of the pin-hole plates are created on the light receiving surface of the photoelectric converting device of the FIG. 1 apparatus in each case.

(1) When the eye $E_1$ to be examined is a spherical surface:

Irrespective of the radius of curvature of the spherical surface, the images of the pair of pin-hole plates 2a and 2b or 2c and 2d are always created in a predetermined direction on the photoelectric converter device 13. That is, when light enters the eye $E_1$ from the direction in which the direction p of the optical axis $O_1$, $O_2$ of each projection optical system and the direction q of the optical axis $O_3$, $O_4$ of each projection optical system are orthogonal to each other, as shown in FIG. 3A, the images 2a', 2b', 2c' and 2d' of the pin-hole plates 2a, 2b, 2c and 2d are created on the light receiving surface of the photoelectric converter device 13, as shown in FIG. 4A. The direction $p_1$ of the images 2a' and 2b' and the direction $q_1$ of the images 2c' and 2d' are orthogonal to each other, and the spacing between the images 2a' and 2b' is equal to the spacing between the images 2c' and 2d'. Also, even if the radius of curvature of the eye $E_1$ varies, the spacings between the images only vary in accordance with the variation in the radius of curvature and the directions $p_1$ and $q_1$ do not vary.

Figure 3B:
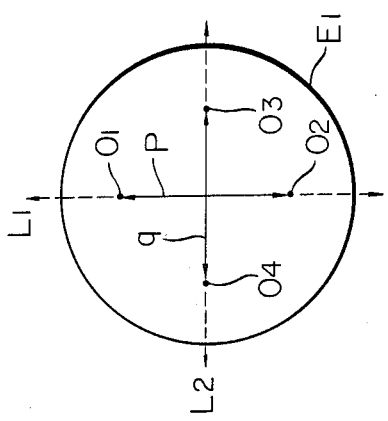
Figure 4B:
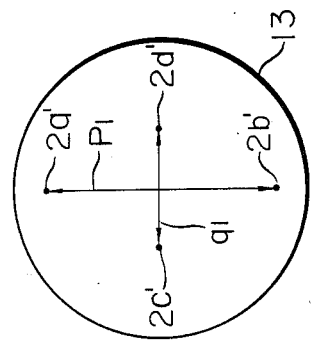

(2) When the eye $E_1$ is a toric surface and the direction of one principal meridian thereof is coincident with the direction p of the optical axis $O_1$, $O_2$ and the direction of the other principal meridian is coincident with the direction q of the optical axis $O_3$, $O_4$:

Irrespective of the radius of curvature in the direction of each principal meridian, the images of the pair of pin-hole plates 2a and 2b or 2c and 2d are always created in a predetermined direction of the photoelectric converter device 13. However, the spacing between the images of the pair of pin-hole plates 2a and 2b or 2c and 2d varies in accordance with the radius of curvature in the direction of each principal meridian. That is, when, as shown in FIG. 3B, the directions $L_1$ and $L_2$ of the principal meridians of the eye $E_1$ are respectively coincident with the direction p of the optical axis $O_1$, $O_2$ of each projection optical system and the direction q of the optical axis $O_3$, $O_4$ of each projection optical system, the images 2a', 2b', 2c' and 2d' of the pin-hole plates 2a, 2b, 2c and 2d are created on the light receiving surface of the photoelectric converter device 13, as shown in FIG. 4B. The direction of the images 2a' and 2b' is coincident with the direction $p_1$ when the eye $E_1$ is a spherical surface, and the direction of the images 2c' and 2d' is coincident with the direction $q_1$ when the eye $E_1$ is a spherical surface. The difference from the case where the eye $E_1$ is a spherical surface is that spacing between the images 2a' and 2b' and the spacing between the images 2d' and 2d' correspond to the radius of curvature in the direction of each principal meridian and therefore are not equal to each other.

Figure 3C:
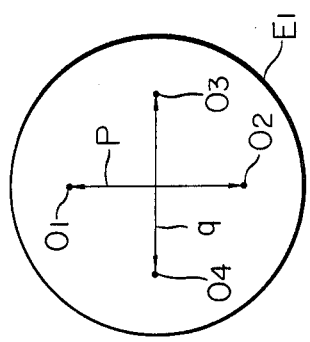
Figure 4C:
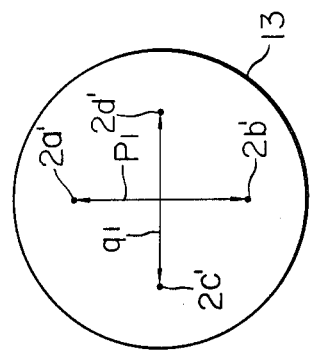

(3) When the eye $E_1$ is a toric surface and the direction of one principal meridian thereof is deviated by a predetermined angle $\alpha$ relative to the direction p of the optical axis $O_1$, $O_2$ and the direction of the other principal meridian is deviated by a predetermined angle $\alpha$ relative to the direction q of the optical axis $O_3$, $O_4$:

The images of the pair of pin-hole plates 2a and 2b or 2c and 2d are created on the photoelectric converter device 13 in a direction $p_2$ or $q_2$ deviated by an angle $\alpha$ relative to the direction $p_1$ or $q_1$ created when the eye $E_1$ is a spherical surface. The spacing between the images 2a' and 2b' and the spacing between the images 2c' and 2d' respectively correspond to the radii of curvature in the directions p and q on the eye $E_1$. That is, when as shown in FIG. 3C, the direction $L_1$ of one principal meridian of the eye $E_1$ is deviated by $\alpha$ relative to the direction p of the optical axis $O_1$, $O_2$ of each projection optical system and the direction $L_2$ of the other principal meridian is deviated by $\alpha$ relative to the direction q of the optical axis $O_3$, $O_4$ of each projection optical system, the images $2a'$, $2b'$, $2c'$ and $2d'$ of the pin-hole plates $2a$, $2b$, $2c$ and $2d$ are created on the light receiving surface of the photoelectric converter device 13, as shown in FIG. 4C. The direction of the images $2a'$ and $2b'$ is a direction $p_1'$ inclined by an angle $\alpha$ relative to the direction $p_1$ when the eye $E_1$ is a spherical surface, and the direction of the images $2c'$ and $2d'$ is a direction $q_1'$ inclined by an angle $\alpha$ relative to the direction $q_1$ when the eye $E_1$ is a spherical surface. The spacing between the images $2a'$ and $2b'$ corresponds to the radius of curvature in the direction p in the eye $E_1$, and the spacing between the images $2c'$ and $2d'$ corresponds to the radius of curvature in the direction q in the eye $E_1$.

Of the above-described cases (1), (2) and (3), the cases (1) and (2) are special cases of the case (3) and generally, it suffices to consider the case (3) and therefore, on the basis of the case (3), the method of processing the signal on the photoelectric converter device 13 according to the present invention will be described.

Figure 5:
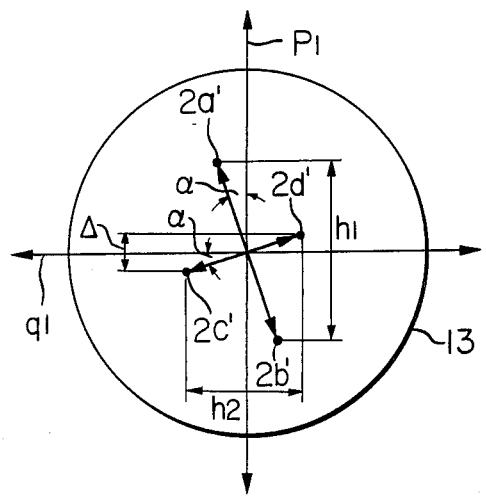
FIG. 5 illustrates a method of processing the signal from the photoelectric converting device.

In the method of the present invention, as shown in FIG. 5, the directions of the two principal meridians of the eye $E_1$ and the radii of curvature in those directions are obtained from the projection distance $h_1$ at which the spacing between the images $2a'$ and $2b'$ has been projected in the direction $p_1$, the projection distance $h_2$ at which the spacing between the images $2c'$ and $2d'$ has been projected in the direction $q_1$, the projection distance $\Delta$ at which the spacing between the images $2a'$ and $2b'$ has been projected in the direction $q_1$ and/or the projection distance $\Delta$ at which the spacing between the images $2c'$ and $2d'$ has been projected in the direction $p_1$. This will hereinafter be described in detail.

A toric surface can be considered with the standard spherical surface and the cylindrical surface being separated from each other. Assuming that the radii of curvature in the directions of the two principal meridians are $H_1$ and $H_2$, it can be considered a cylindrical surface having a radius of curvature $H_1-H_2$ has overlapped, for example, a spherical surface having a radius of curvature $H_1$. In this case, as described in connection with the case (1) above, the spherical surface is uniform in the entire circumferential direction and therefore, if the condition of the cylindrical surface is known, the condition of the toric surface can be known. In FIG. 5, the spacing between the images $2a'$ and $2b'$ corresponds to $(H_1-H_2) \cos \alpha$ relative to the component having a radius of curvature $H_1-H_2$. Accordingly, the spacing when this spacing has been projected in the direction $p_1$ corresponds to $(H_1-H_2) \cos^2 \alpha$. Likewise, the spacing between the images $2c'$ and $2d'$ corresponds to $(H_1-H_2) \sin \alpha$ ($=H_1-H_2) \cos (90+\alpha)$) relative to the component having the radius of curvature $H_1-H_2$. Accordingly, the spacing when this spacing has been projected in the direction $q_1$ corresponds to $(H_1-H_2) \sin^2 \alpha$. Also, the spacing between the images $2c'$ and $2d'$ corresponds to $(H_1-H_2) \sin \alpha$ relative to the component having the radius of curvature $H_1-H_2$ and therefore, the spacing when this spacing has been projected in the direction $p_1$ corresponds to $(H_1-H_2) \sin \alpha \cdot \cos \alpha$.

Therefore, for the spacings $h_1$ and $h_2$ in FIG. 5, with the radius of curvature of the spherical surface taken into account, the following relations are established:

$$h_1 = H_1 + (H_1-H_2) \cos^2 \alpha \quad (1)$$

$$h_2 = H_1 - (H_1-H_2) \sin^2 \alpha \quad (2)$$

(where the proportion constant is 1).

Also, for the spacing $\Delta$, the following relation is established:

$$\Delta = (H_1-H_2) \sin \alpha \cdot \cos \alpha \quad (3)$$

The reason why the component of the spherical surface is not contained in $\Delta$ is that the component of the spherical surface $H_1$ is not included in the projection components of the images $2c'$ and $2d'$ in the direction $p_1$.

From equations (1), (2) and (3), $H_1$, $H_2$ and $\alpha$ can be obtained as follows:

$$H_1 = \frac{h_1 + h_2 + \sqrt{(h_1 - h_2)^2 + (2\Delta)^2}}{2} \quad (4)$$

$$H_2 = \frac{h_1 + h_2 - \sqrt{(h_1 - h_2)^2 + (2\Delta)^2}}{2} \quad (5)$$

$$\alpha = \sin^{-1} \frac{\Delta}{H_1 - H_2} \quad (6)$$

$H_1$ and $H_2$ of equations (4) and (5) just correspond to the spacing between the images $2a'$ and $2b'$ and the spacing between the images $2c'$ and $2d'$ when the direction of one principal meridian is coincident with the direction $p_1$ and the direction of the other principal meridian is coincident with the direction $q_1$.

Accordingly, as is well known, assuming that the radii of curvature in the directions of the two principal meridians are $r_1$ and $r_2$, that the magnification of the optical system is $\beta$ and that the angle formed between the projection optical axis and the objective optical axis is $\theta$, there is the following relation between the above-described spacings $H_1$ and $H_2$:

$$H_1 = \beta r_1 \tan \theta$$

$$H_2 = \beta r_2 \tan \theta$$

and hence, $$r_1 = \frac{1}{\beta \tan \theta} \left\{ \frac{h_1 + h_2 + \sqrt{(h_1 - h_2)^2 + (2\Delta)^2}}{2} \right\} \quad (7)$$

$$r_2 = \frac{1}{\beta \tan \theta} \left\{ \frac{h_1 + h_2 - \sqrt{(h_1 - h_2)^2 + (2\Delta)^2}}{2} \right\} \quad (8)$$

$$\alpha = \tfrac{1}{2} \sin^{-1} \left( \frac{2}{\sqrt{(h_1 - h_2)^2 + (2\Delta)^2}} \right) \quad (9)$$

Since the directions $p_1$ and $q_1$ are known, the directions of the two principal meridians are obtained from the angle $\alpha$ and the radii of curvature in those directions are given by $r_1$ and $r_2$.

The spacings $h_1$, $h_2$ and $\Delta$ may be obtained in any manner, but in the present embodiment, the spacings $h_1$, $h_2$ and $\Delta$ can be automatically obtained by obtaining the coordinates value of the images $2a'$, $2b'$, $2c'$ and $2d'$ by the use of a light image position detecting device and effecting an operational process on the basis of the coordinates value. Accordingly, by connecting an operational device 100 to the position sensor 13, the radius of curvature, etc. of the eye $E_1$ can be displayed on a display device 101.

The radii of curvature $r_1$ and $r_2$ and the angle $\alpha$ may be obtained by carrying out an operation from the obtained spacings $h_1$, $h_2$ and $\Delta$ on the basis of equations (7), (8) and (9), but in the actual apparatus, the combination of the spacings $h_1$, $h_2$ and $\Delta$ primarily gives the radii of curvature $r_1$ and $r_2$ and the angle $\alpha$ and therefore, if sham eyes slightly differing in radii of curvature $r_1$ and $r_2$ and angle $\alpha$ are pre-measured and a correspondence table between the combination of the spacings $h_1$, $h_2$ and $\Delta$ and the combination of the values $r_1$, $r_2$ and $\alpha$ is prepared, it will not be necessary to operate each time. Also, if this idea is extended, even if the pair of light spots are not projected from the orthogonal planes onto the eye $E_1$, or even if the standard directions for obtaining the projection distance are not always orthogonal to each other, or even if the projection directions of the light spots and the standard directions are not in the relation as shown in the above-described embodiment, the relation of 1:1 between the combination of the spacings $h_1$, $h_2$ and $\Delta$ and the combination of the values $r_1$, $r_2$, and $\alpha$ does not change and therefore, the spacings $h_1$, $h_2$ and $\Delta$ can be measured to primarily obtain the values $r_1$, $r_2$ and $\alpha$.

Figure 6:
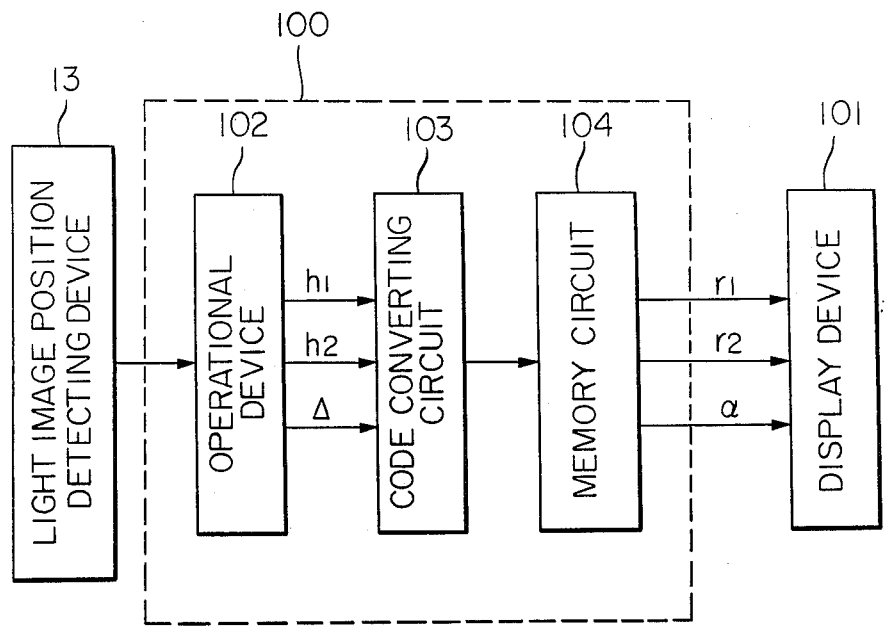
FIG. 6 shows an example of the apparatus block for effecting the signal processing.

As shown in FIG. 6, the signal from the light image position detecting device 13 corresponding to the coordinates value of the images $2a'$, $2b'$, $2c'$ and $2d'$ is operation-processed to the spacings $h_1$, $h_2$ and $\Delta$ by an operational device 102. The signals produced from the operational device 102 which corresponds to the spacings $h_1$, $h_2$ and $\Delta$ are applied as inputs to a code converting circuit 103. The code converting circuit 103 generates a signal for reading out the stored data of a predetermined address of a memory circuit 104 in accordance with the combination of the input signals. The memory circuit 104 stores therein the data $r_1$, $r_2$ and $\alpha$ correspondingly to each address and produces the data stored in the address to which the input has been applied. Thus, the memory circuit 104 to which the signal produced from the code converting circuit 103 has been applied as input generates values $r_1$, $r_2$ and $\alpha$ corresponding to the spacings $h_1$, $h_2$ and $\Delta$ produced from the operational device 102. The display device 101 displays the values $r_1$, $r_2$, and $\alpha$ produced from the memory circuit 104. That is, the display on the display device 101 is the data of the eye $E_1$.

The operational device 102, code converting circuit 103 and memory circuit 104 in FIG. 6 perform the same function as the previously described operational device 100.

In the above-described embodiment, the light image position detecting device 13 is used to obtain the coordinates value of the images $2a'$, $2b'$, $2c'$ and $2d'$, and a second embodiment will now be described which effects measurement without using the light image position detecting device, which is expensive.

Figure 10:
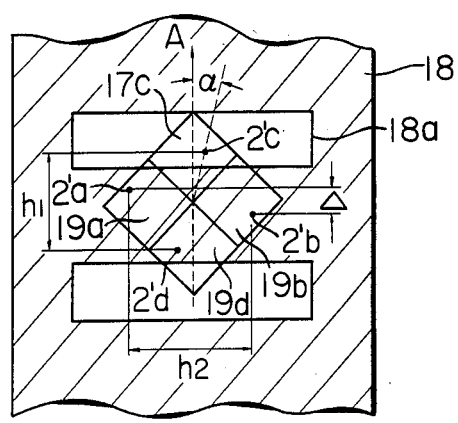
FIG. 10 illustrates the scanning by the chopper of FIGS. 7 and 8.
Figure 11A:
FIGS. 11A and 11B show the output signals of the photoelectric conversion elements.
Figure 11B:
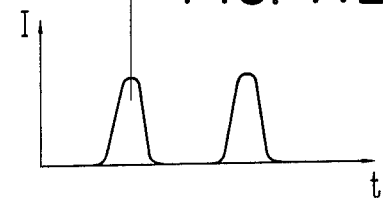

In the second embodiment, elements similar to those in FIGS. 1 to 5 are given similar reference numerals and need not be described. In FIG. 7, the arrow B—B is the same as the arrow A—A of FIG. 1. The light path of objective lenses 4 and 11 is divided into a transmitted light beam and a reflected light beam by a beam splitter 14. The light reflected by the beam splitter 14 is twice reflected after having entered a prism 15, and exits at right angles with the incident light. On the other hand, the light transmitted through the beam splitter 14 is bent at 90° (toward this side of the plane of the drawing sheet of FIG. 7) by a prism 16 and exits from the prism 16. As can be seen from FIG. 8 which is a view taken along arrow B—B of FIG. 7, the light paths of the light beams exiting from the prisms 15 and 16 are orthogonal to each other and perpendicular to the side surface of a drum type chopper 18 rotated at a constant speed by a motor 17. The lengthwise direction of the chopper 18 is the direction orthogonal to the direction of rotation thereof, and the chopper 18 is formed with slits 18a (only some of which are shown in FIG. 7) at predetermined intervals. The light beams passed through the slits of the chopper 18 enter photoelectric converting devices 19 and 20 (the device 20 is not shown in FIG. 7). As shown in FIG. 9A, the photoelectric converting device 19 comprises four independent photoelectric conversion elements 19a, 19b, 19c and 19d, and as shown in FIG. 9B, the photoelectric converting device 20 comprises two independent photoelectric conversion elements 20a and 20b. The photoelectric conversion elements 19a to 19d correspond to pin-hole plates 2a to 2d. The photoelectric conversion elements 20a and 20b correspond to the pin-hole plates 2a and 2b. The chopper 18 in the present embodiment scans the slits on the photoelectric converting device 19 in a direction perpendicular to the plane of the drawing sheet of FIG. 7, namely, a direction passing through the images $2c'$ and $2d'$ of the pin-hole plates 2c and 2d when the eye $E_1$ to be examined is a spherical surface. Also, the chopper 18 scans the slits on the photoelectric converting device 20 in a direction passing through the images $2a'$ and $2b'$ of the pin-hole plates 2a and 2b. When the eye $E_1$ is a toric surface, the images $2a'$ to $2d'$ of the pin-hole plates are subjected to the influence of the twist by the eye $E_1$ and, as shown in FIG. 10, for example, the direction of the images $2c'$ and $2d'$ becomes deviated from the scanning direction of the slits (arrow A) by an angle $\alpha$ corresponding to said twist. The photoelectric conversion element 19d produces a high level signal only when the slits of the chopper 18 lie just on the image $2d'$ of the pin-hole plate and therefore, the output signal of the photoelectric conversion element 19d is a pulse signal produced at each predetermined interval (determined by the pitch of the slits and the rotational speed of the chopper) as shown in FIG. 11A by rotation of the chopper 18. Likewise, the output signal of the photoelectric conversion element 19c is a signal as shown in FIG. 11B. Even if the direction of the images $2c'$ and $2d'$ becomes deviated by a predetermined angle under the influence of the twist, the scanning direction of the slits does not change and therefore, the time $t_1$ (see FIGS. 11A and 11B) from after the pulse of the photoelectric conversion element 19d (FIG. 11A) has been produced until the pulse of the photoelectric conversion element 19c is produced becomes the spacing $h_1$ (see FIG. 10) in which the spacing between the images $2c'$ and $2d'$ has been projected in the scanning direction of the slits on the photoelectric converting device 19. Also, the time (see FIGS. 11A and 11B) from after the pulse of the photoelectric conversion element 19b has been produced until the pulse of the photoelectric conversion element 19a is produced corresponds to the spacing $\Delta$ in which the spacing between the images $2a'$ and $2b'$ has been projected in the scanning direction of the slits on the photoelectric converting device 19. Likewise, the time (not shown) from after the pulse of the photoelectric conversion element 20a has been produced on the photoelectric converting device 20 until the pulse of the photoelectric conversion element 20b is produced corresponds to the spacing $h_2$ (tentatively shown in FIG. 10) in which the spacing between the images 2a' and 2b' has been projected in the scanning direction of the slits on the photoelectric converting device 20. The spacing $h_2$ is equal to the spacing in which, in FIG. 10, the spacing between the images 2a' and 2b' has been projected in a direction orthogonal to the scanning direction (arrow A) of the slits on the photoelectric converting device 19. The deviation between the images 2c' and 2d' is equal to the deviation between the images 2a' and 2b' (as is well known, the direction of the images 2a' and 2b' is always perpendicular to the direction of the images 2c' and 2d') and therefore is the same as the spacing $\Delta$ in which the spacing between the images 2c' and 2d' has been projected in the scanning direction of the slits on the photoelectric converting device 20 and thus, it is not measured in the present embodiment.

As shown in FIG. 12, the output signals of the photoelectric conversion elements 19a to 19d and 20a, 20b are amplified by amplifier circuits 190a to 190d and 200a, 200b corresponding thereto. The output signals of the amplifier circuits 190a and 190b are applied as inputs to a first time difference measuring circuit 21, the output signals of the amplifier circuits 190c and 190d are applied as inputs to a second time difference measuring circuit 22, and the output signals of the amplifier circuits 200a and 200b are applied as inputs to a third time difference measuring circuit 23. Each of the time difference measuring circuits 21, 22 and 23 produces a signal corresponding to the time difference between the two input signals (pulses). The output signal of the first time difference measuring circuit 21 is converted into a signal corresponding to the spacing $h_1$ by a first converting circuit 24, the output signal of the second time difference measuring circuit 22 is converted into a signal corresponding to the spacing $\Delta$ by a second converting circuit 25, and the output signal of the third time difference measuring circuit 23 is converted into a signal corresponding to the spacing $h_2$ by a third converting circuit 26. The output signals $h_1$, $h_2$ and $\Delta$ of the first to third converting circuits 24, 25 and 26 are applied as inputs to an operational device 257. The operational device 257 determines the radius of curvature $r_1$ in the direction of one principal meridians, the radius of curvature $r_2$ in the direction of the other principal meridian and the angle of twist $\alpha$ (this is an angle which determines the directions of the principal meridians), as follows, using the pre-introduced magnification $\beta$ of the optical system, the angle $\theta$ formed between the optical axis of the objective lens and the optical axis of the projection optical system, a constant k (in the first embodiment, k=1) and the output signals $h_1$, and $h_2$ and $\Delta$ of the first to third converting circuits 24, 25 and 26:

$$r_1 = \frac{1}{k\beta\tan\theta}\left\{\frac{(h_1 + h_2) + \sqrt{(h_2 - h_1)^2 + (2\Delta)^2}}{2}\right\} \quad (10)$$

$$r_2 = \frac{1}{k\beta\tan\theta}\left\{\frac{(h_1 + h_2) - \sqrt{(h_2 - h_1)^2 + (2\Delta)^2}}{2}\right\} \quad (11)$$

$$\alpha = \frac{1}{2}\sin^{-1}\left(\frac{2\Delta}{\sqrt{(h_2 - h_1)^2 + (2\Delta)^2}}\right) \quad (12)$$

The thus determined radii of curvature $r_1$ and $r_2$ and angle of twist $\alpha$ are produced from the operational device 257 and applied as inputs to the display device 101, which displays these values. The display device may produce a numerical display employing seven-segment display elements, for example, and may include a printer to provide a permanent record. Since the directions of the pair of projection optical systems are known, the directions of the principal meridians can be determined from $\alpha$ given by equation (12). The above-mentioned constant k is a value determined by the scanning speed of the slits, etc. and may be obtained by an experiment after the apparatus has been assembled.

The operation of the apparatus will hereinafter be described.

Figure 13A:
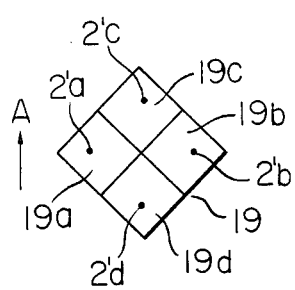
FIGS. 13A, 13B, 14A and 14B illustrate the operation of the second embodiment.
Figure 13B:
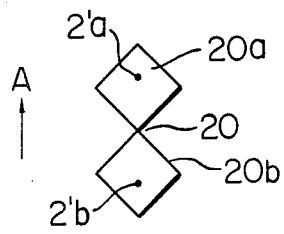

First, if the eye $E_1$ to be examined is a spherical surface, as shown in FIG. 13A, on the photoelectric converting device 19, the direction passing through the images 2a' and 2b' of the pin-hole plates is orthogonal to the scanning direction A of the slits and the direction passing through the images 2c' and 2d' of the pin-hole plates is coincident with the scanning direction A of the slits. Also, on the photoelectric converting device 20, the direction passing through the images 2a' and 2b' of the pin-hole plates is coincident with the scanning direction A of the slits (see FIG. 13B). Accordingly, the first converting circuit 24 and the third converting circuit 26 produce signals corresponding to the radii of curvature on the eye $E_1$ along the scanning directions of the slits on the photoelectric converting devices 19 and 20 (which are optically coincident with the directions of the pair of projection optical systems because there is no twist influence by the eye $E_1$), namely, a signal representative of the spacing $h_1$ between the images 2c' and 2d' of the pin-hole plates and a signal representative of the spacing $h_2$ (=$h_1$) between the images 2a' and 2b' of the pin-hole plates. (Since the eye $E_1$ is a spherical surface, the spacings, namely, the radii of curvature, are equal in the directions of all diametral lines.) On the other hand, the second converting circuit 25 generates a zero signal ($\Delta=0$). Therefore, the operational device 257 determines the radius of curvature r and the angle of twist $\alpha$ as follows by the above-mentioned equations (10), (11) and (12):

$$r = r_1 = r_2 = \frac{h_2}{k\beta\tan\theta}$$

$$\alpha = 0$$

Next, when the eye $E_1$ has a toric surface and the directions of the principal meridians thereof lie in a plane containing the pair of projection optical systems, the first converting circuit 24 and the third converting circuit 26 respectively generate a signal representative of the spacing $h_1$ between the images 2c' and 2d' of the pin-hole plates and a signal representative of the spacing $h_2$ between the images 2a' and 2b' of the pin-hole plates. Therefore, the operational device 257 determines the radii of curvature $r_1$ and $r_2$ and the angle of twist $\alpha$ as follows by the above-mentioned equations (10), (11) and (12):

$$r_1 = \frac{h_2}{k\beta\tan\theta}$$

$$r_2 = \frac{h_1}{k\beta\tan\theta}$$

$$\alpha = 0$$

When the angle of twist $\alpha$ is zero, the directions of the principal meridians are the direction of the line of intersection between the plane containing the pair of projection optical systems and the surface of the eye $E_1$. Since the direction of the plane containing the pair of projection optical systems is known, the directions of the principal meridians of the eye $E_1$ can be obtained.

Figure 14A:
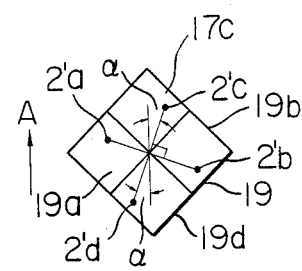
Figure 14B:
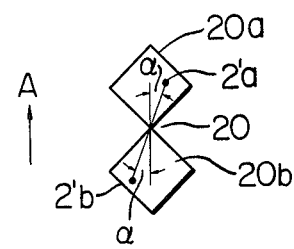

Also, when the eye $E_1$ has a toric surface and the directions of the principal meridians thereof are twisted by an angle $\alpha$ relative to the plane containing the pair of projection optical systems, as shown in FIGS. 14A and 14B, the direction of the images $2a'$ and $2b'$ of the pinhole plates on the photoelectric converting device 20 and the direction of the images $2c'$ and $2d'$ of the pinhole plates on the photoelectric converting device 19 are deviated by an angle $\alpha$ relative to the scanning direction of the slits on each device. In this case, as previously described, the directions of the two principal meridians and the radii of curvature in those directions can be obtained by equations (10), (11) and (12).

As described above, the operational device 257 may have the function of performing the operations of equations (10), (11) and (12), but as shown in the example of FIG. 6, the curvature of the eye $E_1$ is primarily determined by the values $h_1$, $h_2$ and $\Delta$ and therefore, sham eyes whose twist and radii of curvature are known may be prepared at predetermined intervals and they may be measured by the apparatus and, correspondingly to the then signals $h_1$, $h_2$ and $\Delta$, the twist $\alpha$ and the radii of curvature $r_1$ and $r_2$ in the directions of the two principal meridians of the sham eyes may be stored in a memory device so as to correspond to each other, and the signals $h_1$, $h_2$ and $\Delta$ when the eye $E_1$ to be examined has been measured may be used as the address designating signals of the memory device. That is, when the measured values are certain signals $h_1$, $h_2$ and $\Delta$, the twist and radii of curvature pre-measured for the sham eyes are stored in the memory portion whose address is designated by the combination of said signals and therefore, if the design is such that the radii of curvature, etc. are obtained by reading out the stored data, the operational device 257 will not have to perform the so-called arithmetic operation during each measurement. Particularly, in a human eye, the distribution of curvature is within a relatively narrow range and therefore, in an ophthalmometer, it will be convenient if the operational device 257 is so designed.

As is apparent from the foregoing description, the unknown quantities are values $r_1$, $r_2$ and $\alpha$ and three relations are established among the three measured values $h_1$, $h_2$ and $\Delta$ and therefore, for example, as in the above-described embodiment, the directions of the pair of projection optical systems need not be orthogonal to each other if they are known and also, when the eye $E_1$ is a spherical surface, the images of the pair of pin-hole plates created on the photoelectric converting devices 19 and 20 need not be coincident with the scanning direction of the slits. In this case, however, it is necessary that the amount of deviation be known. This also holds true of the first embodiment.

According to the present invention, as has been described above, not only is it possible to automatically obtain the directions of the principal meridians of an object to be examined (a human eye, a lens or the like) and the radii of curvature in those directions, but also it is possible to obtain the radii of curvature without rotating the apparatus, and this provides a curvature radius measuring apparatus which is very easy to use.

I claim:

1. An automatic apparatus for measuring radius of curvature, including:
    (a) measuring optical means having an objective lens;
    (b) first projection optical means for projecting a first pair of light spots onto an object to be examined from two respective directions symmetric with respect to the optical axis of said objective lens;
    (c) second projection optical means for projecting a second pair of light spots onto said object from two respective directions symmetric with respect to the optical axis of said objective lens and discrete from the spots and directions of said first projection optical system;
    (d) light image position detecting means for receiving through said objective lens reflected light from said four light spots reflected by said object, said detecting means being disposed at a predetermined position on the optical axis of said measuring optical means and in a plane orthogonal to said optical axis and producing signals corresponding to the positions thereon of images of the light spots formed by said objective lens; and
    (e) operation and display means for obtaining from said signals at least three, and no more than four, of the spacings between the images of the light spots of said first pair and between the images of the light spots of said second pair along two predetermined directions different from each other which lie in said plane, and for determining, based on said spacings, and displaying an angle which determines the directions of the principal meridians of said object and the radii of curvature in those directions.

2. The apparatus according to claim 1, wherein said light image position detecting means includes two-dimensional light image position detecting means disposed at the position of a reflection image created by said measuring optical means after the first and second pairs of light spots have been reflected by said object.

3. The apparatus according to claim 1, wherein said light image position detecting means includes a photoelectric converting device having at least two pairs of photoelectric conversion elements disposed adjacent to each other on the same plane and corresponding to said pairs of light spots, and scanning means having a light intercepting member of predetermined width and alternately scanning the light receiving surfaces of said pairs of photoelectric conversion elements at a predetermined speed in said two predetermined directions by said light intercepting member, and wherein said operation and display means has means for obtaining said spacings by adding the width and scanning speed of said light intercepting member to the time difference between the width and scanning speed of said light intercepting member and the photoelectric conversion signals from said pairs of photoelectric conversion elements.

4. The apparatus according to claim 3, wherein said first projection optical means includes a first optical system and a second optical system having projection optical axes symmetrically to the optical axis of said objective lens, said second projection optical means includes a third optical system and a fourth optical system having projection optical axes symmetrically to the optical axis of said objective lens, and said third and fourth optical systems have their positional relation with said first and second optical systems determined so that:
   (a) a plane containing said third and fourth optical systems is orthogonal to a plane containing said first and second optical systems, the line of orthogonality being coincident with the optical axis of said objective lens;
   (b) the angle formed by said third and fourth optical systems with the optical axis of said objective lens is equal to the angle formed by said first and second optical systems with the optical axis of said objective lens; and
   (c) the position whereat said third and fourth optical systems intersect the optical axis of said objective lens is coincident with the position whereat said first and second optical systems intersect the optical axis of said objective lens.

5. An automatic apparatus for measuring radius of curvature, including:
   (a) measuring optical means having an objective lens;
   (b) first projection optical means for projecting a first pair of light spots onto an object to be examined from two respective directions symmetric with respect to the optical axis of said objective lens;
   (c) second projection optical means for projecting a second pair of light spots onto said object from two respective directions symmetric with respect to the optical axis of said objective lens and discrete from said first projection optical system;
   (d) light image position detecting means for receiving through said objective lens reflected light from said four light spots reflected by said object, said detecting means being disposed at a predetermined position on the optical axis of said measuring optical means and in a plane orthogonal to said optical axis and producing signals corresponding to the positions thereon of images of the light spots formed by said objective lens; and
   (e) operation and display means for obtaining from said signals at least three, and no more than four, of the spacings between the images of the light spots of said first pair and between the images of the light spots of said second pair along two predetermined directions which lie in said plane, and for determining, based on said spacings, and displaying the directions of the principal meridians of said object and the radii of curvature in those directions,
   wherein said first projection optical means includes a first optical system and a second optical system having projection optical axes symmetrically to the optical axis of said objective lens, said second projection optical means includes a third optical system and a fourth optical system having projection optical axes symmetrically to the optical axis of said objective lens, and said third and fourth optical systems have their positional relation with said first and second optical systems determined so that:
   (a) a plane containing said third and fourth optical systems is orthogonal to a plane containing said first and second optical systems, the line of orthogonality being coincident with the optical axis of said objective lens;
   (b) the angle formed by said third and fourth optical systems with the optical axis of said objective lens is equal to the angle formed by said first and second optical systems with the optical axis of said objective lens; and
   (c) the position whereat said third and fourth optical systems intersect the optical axis of said objective lens is coincident with the position whereat said first and second optical systems intersect the optical axis of said objective lens,
   wherein said light image position detecting means includes a photoelectric converting device having at least two pairs of photoelectric conversion elements disposed adjacent to each other on the same plane and corresponding to said pairs of light spots, and scanning means having a light intercepting member of predetermined width and alternately scanning the light receiving surfaces of said pairs of photoelectric conversion elements at a predetermined speed in said two predetermined directions by said light intercepting member,
   wherein said operation and display means has means for obtaining said spacings by adding the width and scanning speed of said light intercepting member to the time difference between the width and scanning speed of said light intercepting member and the photoelectric conversion signals from said pairs of photoelectric conversion elements, and wherein said operation and display means carries out the following operations by the values of the projection spacing $h_1$ in which the spacing between the images of one pair of light spots has been projected in one of said two predetermined directions, the projection spacings $h_2$ and $\Delta$ in which the spacing between the images of the other pair of light spots has been projected in said two predetermined directions, the radii of curvature $r_1$ and $r_2$ in the directions of the principal meridians of said object, and the angle of twist $\alpha$:

$$r_1 = \frac{1}{k\beta\tan\theta}\left\{\frac{(h_1 + h_2) + \sqrt{(h_1 - h_2)^2 + (2\Delta)^2}}{2}\right\}$$

$$r_2 = \frac{1}{k\beta\tan\theta}\left\{\frac{(h_1 + h_2) - \sqrt{(h_1 - h_2)^2 + (2\Delta)^2}}{2}\right\}$$

$$\alpha = \tfrac{1}{2}\sin^{-1}\left(\frac{2\Delta}{(h_1 - h_2)^2 + (2\Delta)^2}\right)$$

where
k: proportion constant
$\beta$: magnification of said measuring optical system
$\theta$: the angle formed between the optical axis of said objective leans and the direction in which the light spots of said first and second projection optical systems are projected.

6. An automatic apparatus for measuring radius of curvature, including:
   (a) measuring optical means having an objective lens;
   (b) first projection optical means for projecting a first pair of light spots onto an object to be examined from two respective directions symmetric with respect to the optical axis of said objective lens;

(c) second projection optical means for projecting a second pair of light spots onto said object from two respective directions symmetric with respect to the optical axis of said objective lens and discrete from said first projection optical system;

(d) light image position detecting means for receiving through said objective lens reflected light from said four light spots reflected by said object, said detecting means being disposed at a predetermined position on the optical axis of said measuring optical means and in a plane orthogonal to said optical axis and producing signals corresponding to the positions thereon of images of the light spots formed by said objective lens; and (e) operation and display means for obtaining from said signals at least three, and no more than four, of the spacings between the images of the light spots of said first pair and between the images of the light spots of said second pair along two predetermined directions which lie in said plane, and for determining, based on said spacings, and displaying the directions of the principal meridians of said object and the radii of curvature in those directions, wherein said light image position detecting means includes a photoelectric converting device having at least two pairs of photoelectric conversion elements disposed adjacent to each other on the same plane and corresponding to said pairs of light spots, and scanning means having a light intercepting member of predetermined width and alternately scanning the light receiving surfaces of said pairs of photoelectric conversion elements at a predetermined speed in said two predetermined directions by said light intercepting member, and wherein said operation and display means has means for obtaining said spacings by adding the width and scanning speed of said light intercepting member to the time difference between the width and scanning speed of said light intercepting member and the photoelectric conversion signals from said pairs of photoelectric conversion elements, and wherein said measuring optical means has light path dividing means disposed between said objective lens and the imaging plane of said measuring optical means for dividing the light path of said measuring optical means into directions orthogonal to each other in a plane orthogonal to said optical axis, said light image position detecting means has said two pairs of photoelectric conversion elements in one of the imaging planes of said divided light paths and at least one pair of photoelectric conversion elements corresponding to one of the pairs of light spots in the other imaging plane, said scanning means has a rotatable drum rotatable about said optical axis and disposed so that the circumference of said rotatable drum intersects said divided light paths, the circumference of said rotatable drum being formed with light-transmitting portions equally spaced apart in the direction of rotation of the drum, and said operation and display means determines said projection spacings from the time difference between signals obtained from each of said two pairs of photoelectric conversion elements and the time difference between signals obtained from said one pair of photoelectric conversion elements.

* * * * *